(12) United States Patent
Dinten et al.

(10) Patent No.: US 7,031,427 B2
(45) Date of Patent: Apr. 18, 2006

(54) METHOD FOR ESTIMATING A SCATTERED RADIATION, PARTICULARLY TO CORRECT TOMOGRAPHY OR BONE DENSITOMETRY MEASUREMENTS

(75) Inventors: Jean-Marc Dinten, Lyons (FR); Michel Darboux, Grenoble (FR)

(73) Assignee: Commissariat a l'Energie Atomique, Paris (FR)

( * ) Notice: Subject to any disclaimer, the term of this patent is extended or adjusted under 35 U.S.C. 154(b) by 0 days.

(21) Appl. No.: 10/644,367

(22) Filed: Aug. 20, 2003

(65) Prior Publication Data

US 2005/0078787 A1 Apr. 14, 2005

(30) Foreign Application Priority Data

Aug. 20, 2002 (FR) .................................. 02 10422

(51) Int. Cl.
*G01N 23/00* (2006.01)
(52) U.S. Cl. ............................................. 378/7; 378/18
(58) Field of Classification Search .................... 378/7, 378/62, 98.4, 6, 18, 86–87, 8
See application file for complete search history.

(56) References Cited

U.S. PATENT DOCUMENTS

| | | | |
|---|---|---|---|
| 4,549,307 A | 10/1985 | Macovski | |
| 5,615,279 A * | 3/1997 | Yoshioka et al. | ........... 382/131 |
| 5,666,391 A | 9/1997 | Ohnesorge et al. | |
| 5,774,521 A | 6/1998 | Close et al. | |
| 6,000,847 A | 12/1999 | Close et al. | |
| 6,594,338 B1 * | 7/2003 | Darboux et al. | ........... 378/98.4 |
| 2002/0048339 A1 | 4/2002 | Schneider et al. | |

FOREIGN PATENT DOCUMENTS

| | | |
|---|---|---|
| FR | 01 02139 | 2/2001 |
| FR | 2820956 | 8/2002 |
| WO | WO 02/26133 A1 | 4/2002 |

OTHER PUBLICATIONS

B.J. Kirby, J.R. Davis, J.A. Grant and M.J. Morgan, "Monochromatic Microtomographic Imaging of Osteoporotic Bone", Jul. 1997, pp. 1375-1385.

(Continued)

*Primary Examiner*—David V. Bruce
*Assistant Examiner*—Hoon Song
(74) *Attorney, Agent, or Firm*—Pearne & Gordon LLP

(57) ABSTRACT

The image of an object is improved by estimating the scattered radiation that it transmits to the detectors. To achieve this, one uses the scattered radiation effectively measured through an imitation of the object, having analogous attenuation properties, and which one modifies by the weighting coefficients obtained by a transformation of the values of the total radiation received through the object (3) and the selected imitation (8). One thus manages to improve the image without subjecting the object to a double irradiation in order to measure the scattered radiation separately. The principal applications are tomography, bone densitometry and non-destructive controls.

11 Claims, 2 Drawing Sheets

OTHER PUBLICATIONS

V.L. Syrmos, J. Yin, D.Y.Y. Yun and P. Misra, "The Photon Diffusion Equations: Forward and Inverse Problems", Aug. 1997, pp. 52-57.

L.G. Hitlz and B.T.A. McKee, "A Source and Object Dependent Scatter Correction Method for Transmission and Emission Imaging", Oct. 1993, pp. 1600-1604.

* cited by examiner

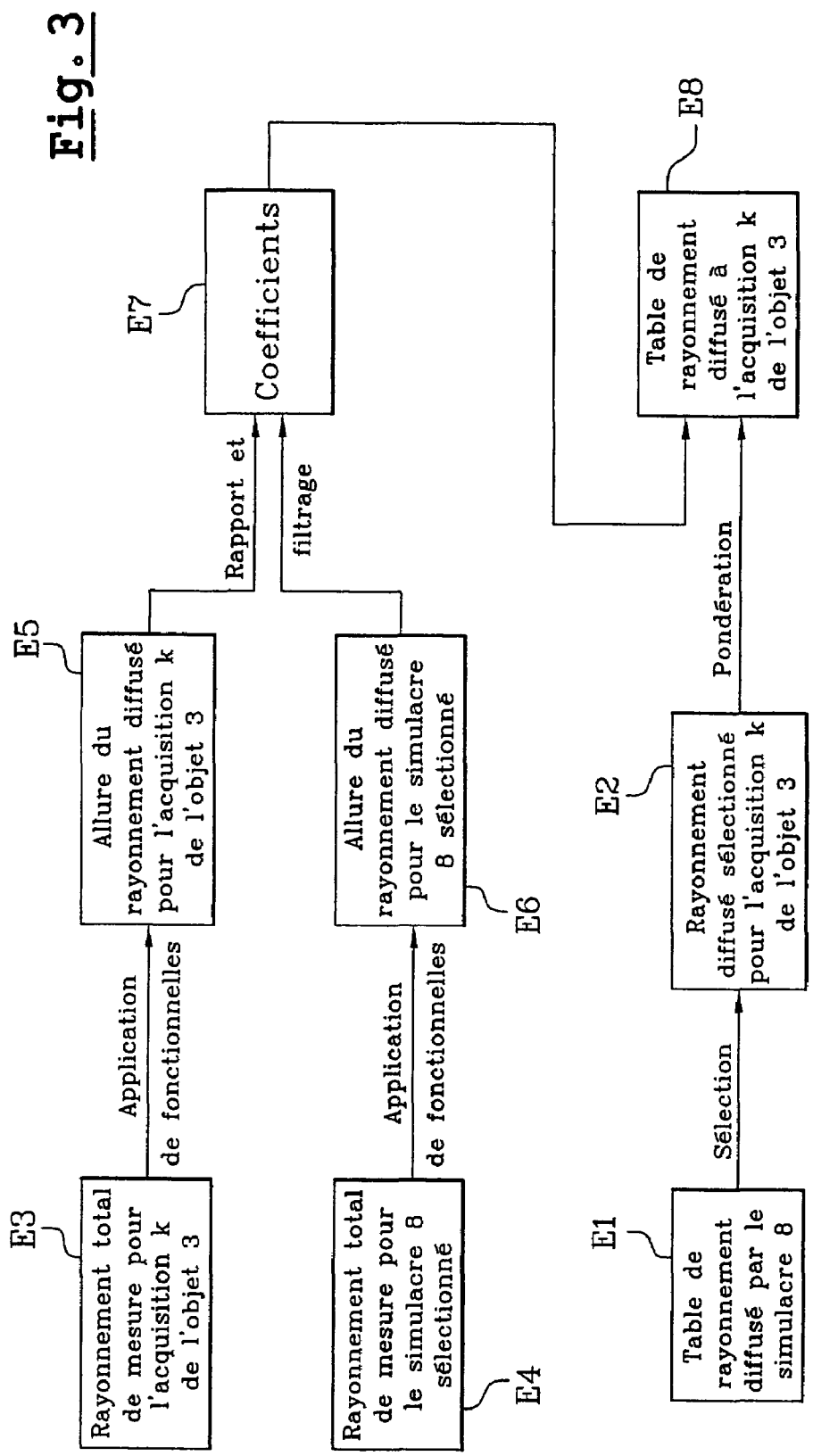

METHOD FOR ESTIMATING A SCATTERED RADIATION, PARTICULARLY TO CORRECT TOMOGRAPHY OR BONE DENSITOMETRY MEASUREMENTS

TECHNICAL FIELD OF THE INVENTION

This invention concerns a method for estimating a scattered radiation, for which the main envisaged application is the correction of tomography or bone densitometry measurements.

BACKGROUND OF THE INVENTION

The use of an irradiation radiation has the disadvantage of producing significant scattered radiation through the examined object, especially in the very frequent event of a diverging radiation (conical or fan shaped). In other words, each of the detectors situated behind the object receive not only a primary radiation, arising directly from the source by a rectilinear path and having crossed through a well defined region of the object, but also a scattered radiation from an indeterminate source which affects the measurement and which it would therefore be desirable to correct.

Several methods are already used. It is in this way that the primary radiation can be measured alone if a rigorous collimation of the detectors and the source is made in order to intercept the scattered radiation, but in practice said method requires a scanning of the beam, which takes time to accomplish, and during which one has to put up with movements of the patient, if one is examining living organisms.

The opposite idea of only measuring the scattered radiation has also been proposed. To do this, one arranges a discontinuous network of absorbers, such as lead balls, between the object and the detectors, in order to locally stop the primary radiation, in such a way that the detectors located behind said absorbers only measure the scattered radiation. This process, called the "beam stop" process, therefore gives two dimensional tables or bundles of the value of scattered radiation, which one completes by interpolation between the detectors located behind the absorbers. The scattered radiation estimated in this manner is subtracted from the total radiation measured separately. This process is precise but has the disadvantage that it imposes two irradiations of the object and thus the object receives double the dose of radiation. A final example of a method for correcting the scattered radiation by material means comprises the use of anti-scattering grids, but they are only partially efficient; it is insufficient for a conical beam, where the scattered radiation may be several times greater than the primary radiation.

Finally, a certain number of digital methods exist for estimating the scattered radiation, from convolutions and deconvolutions of measurements, for example: one could also cite French patent 2 759 800 for a different, analytical digital method. Said methods are, in general, difficult to employ since they depend on parameters chosen by the user (convolutions kernel, for example) that only give good results in favorable situations, such as small areas where the scattered radiation is low, or objects with a relatively homogeneous content. No simple method exists that makes it possible, for example, to correct the scattered radiation through the thorax or other major anatomical regions, which are frequently examined but which are unfavorable for correcting the scattered radiation due to their very volume and the heterogeneity due to the presence of a complex bone structure and in which the radiation attenuation capacity is very different to that of soft tissue.

Finally, we should mention American U.S. Pat. No. 6,018, 565 which describes a mixed method, using "beam stop" and convolution.

SUMMARY OF THE INVENTION

An essential aim of the invention is to propose a method for estimating and correcting scattered radiation that could be suited to difficult situations of non-destructive control of inert or animate objects, or all image reconstruction methods.

The method according to the invention is, in its most general form, an object imaging method by multiple acquisition, comprising an estimation of a scattered radiation from an initial radiation that has passed through an object while undergoing an attenuation that allows a total measurement radiation to pass through, characterised by:
- for at least one acquisition, taking a table of measurements of a scattered radiation, obtained by passing the initial radiation through an imitation of the object,
- and for each of the acquisitions, calculating transposition coefficients between the imitation and the object, from the initial radiation, the total measurement radiation through the object and a total measurement radiation through the imitation.
- and weighting of the table of measurements with the transposition coefficients.

Advantageously, the imitation will be a block of constant thickness and in a homogeneous material, with an attenuation similar to a base material of the object; in general, the taking of a table of measurements will be a selection in a series of tables of measurements of scattered radiation, obtained beforehand by successively passing the initial radiation through a respective series of imitations of the object, of different but constant thicknesses; and the selection will be made by comparing a value of the total measurement radiation through the object and a value of the total measurement radiation through the imitations.

The weighting coefficients are generally ratios of values of a same functional calculated for the object and for the imitation. The functional used may be equal to the product of the total measurement radiation times the logarithm of the ratio of the total measurement radiation and the initial radiation.

BRIEF DESCRIPTION OF THE DRAWINGS

The invention will now be described in referring to the figures, in which:

and FIG. 3 illustrates the steps of the method.

DESCRIPTION OFF AN EXAMPLE EMBODIMENTS

Figure 1:
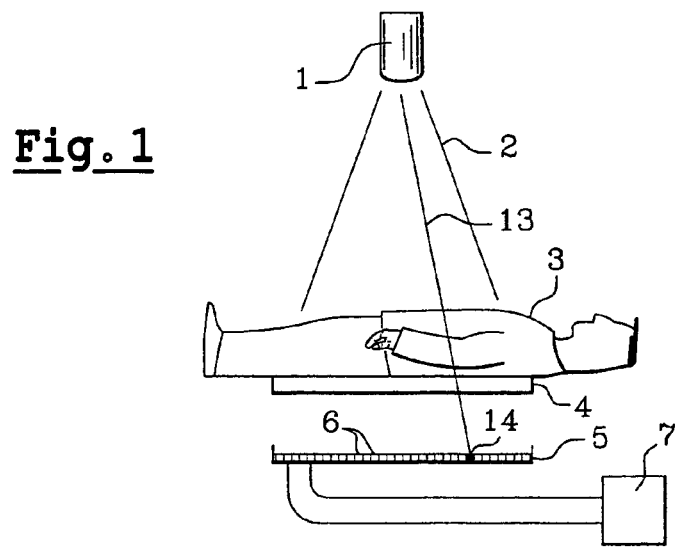
FIG. 1 is a general view of an acquisition of measurements.

We will first refer to FIG. 1, where an X-ray tube 1 emits a conical beam 2 towards an object 3 to be examined (here a patient stretched out on a table 4) then, through him, towards a flat network 5 of detectors 6 arranged in a matrix. The detectors 6 are connected to an acquisition device 7 and measure a scattered radiation that is superimposed on the primary radiation, only suitable for the examination or the control of the object.

Figure 2:
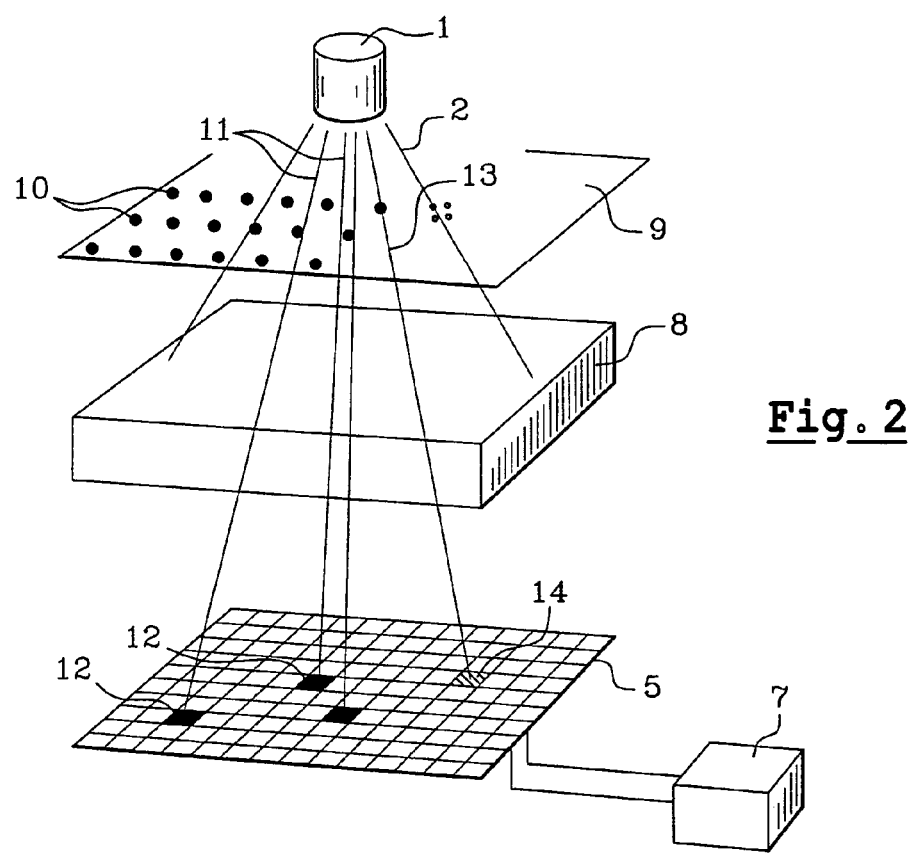
FIG. 2 is a view of a calibration acquisition.

The estimation of the scattered radiation through the patient (object 3) consists firstly in obtaining two dimensional tables or bundles of scattered radiation obtained under comparable circumstances. To achieve this, one carries out calibration radiations through imitations 8 of the object 3 to be examined, in accordance with FIG. 2: the irradiation conditions remain the same, in other words one continues to use the tube 1, the beam 2, the network 5 of detectors 6 and the acquisition device 7, the imitation 8 however replacing the patient; we have also added a grid 9 of lead balls 10 between the imitation 8 and the network 5. It ensues from this arrangement that the rays 11 going through the balls 10 are completely absorbed and the regions 12 of the network 5 located in the same line as said rays 11 have detectors 6 that only measure the scattered radiation at these places. One only has to record these measured values and interpolate between the regions 12 in order to suitably estimate the scattered radiation from the imitation 8 for all of the detectors 6 of the network 5.

The imitation 8 should be similar to the object in order that the radiation scattered by them are identical. A perfect similarity is not possible, and for this reason one makes do with an imitation 8 resembling the object 3 and for which the associated bundle of scattered radiation will be corrected later in order to evaluate that of the object. In practice, the imitation 8 may be a block of a homogeneous material and which has the same attenuation coefficient as the base material of the object 3: in the case of a human body, essentially composed of soft tissue, it is known that Plexiglas (polymethacrylate) is suitable.

In order to allow varied measurements, in reality one will use several bundles of scattered radiation, obtained for as many imitations 8, which will only differ by their thickness and therefore by the length of the path covered by the rays 11. Said bundles are recorded in a data base before the useful measurements on the objects 3, in order to take a bundle of scattered radiation comparable to that of an object 3, one will select in practice one of the bundles of the data base or, even better, a bundle that has been obtained by interpolation calculations between two of said bundles. The selection criterion could be defined by means of a specific ray 13 ending up in a region 14 of the network 5 and which will not pass through either the absorbers 10 of FIG. 2, or through the bone tissues of the patient (or more generally portions of the object 3 in which the absorption properties are different to the material of the imitation 8) in FIG. 1. The total radiation, primary and scattered, received by the region 14 after having crossed each imitation 8 will act as index to the corresponding scattered radiation table, and the selected table will have the index at an identical value to the total radiation measured at region 14 through the object 3. This all corresponds to going from the state E1 to the state E2 in the block diagram of FIG. 3, that we will now begin to explain.

The continuation of the method essentially consists in the correction of the table of scattered radiation thus selected to adjust it as best as possible to the bundle of radiation actually scattered by the object 3. To achieve this, one uses all of the information available, in other words the total radiation received by the detectors 6 beyond the object 3 as the selected imitation 8. Said total radiation is designated $\Phi t$, the scattered radiation $\Phi d$, the initial radiation from the tube $\Phi o$ and the primary radiation $\Phi$, the relation $\Phi t = \Phi + \phi d$ is met.

One is then in states E3 and E4 of the block diagram of FIG. 3. Then, one transforms the total radiation values $\Phi t$ measured for the object 3 and the selected imitation 8 by applying the functionals to them. More precisely, it is know in the art that $\Phi d$ is proportional to $\Phi \log(\Phi/\Phi o)$; this relation, which is called the Klein and Nishina law, gives a general appearance of the scattered radiation, for lack of its intensity.

The initial radiation $\Phi o$ is known; the primary radiation $\Phi$ is not known, but one agrees to apply this relation in an approximate manner by replacing it by the total radiation $\Phi t$, in other words the functional employed associates each measured value of the total radiation $\Phi t$ with the calculated value $\Phi t \log(\Phi t/\Phi o)$, assumed to be close to the scattered radiation $\Phi d$ at this location; we have reached states E5 and E6 in the block diagram.

The following step consists in carrying out, for each of the detectors 6, the ratio of values given by the functional for the object 3 and the imitation 8 selected according to the formula $K = \Phi t \log(\Phi t/\Phi o)$ object/$\Phi t \log(\Phi t/\Phi o)$ imitation. The weighting coefficients K thus obtained will serve to deform the bundle of selected scattered radiation in state E2 in order to estimate that of the object 3. The results again constitute a two dimensional table or a matrix having identical dimensions to that of the radiation tables since it is associated with the network 5 of detectors 6. It is therefore possible and advantageous to carry out a spatial digital filtering of this matrix by applying a low pass filter that corrects the coefficients K while only conserving the lowest frequencies of their variation and thus making them probably closer to reality since the scattered radiation varies quite slowly from one point to another.

When the table of definitive weighting coefficients, designated K', has been obtained (in state E7), it serves to weight the selected table of scattered radiation before state E2, in order to obtain a table of radiation scattered by the object 3 (state E8, which constitutes the sought after estimation); the formula applied is $\Phi d$ object=$K' \Phi d$ object. These estimated object values $\Phi d$ may then be subtracted from the total radiation $\Phi t$ measured by the detectors 6 to estimate the primary radiation $\Phi$ and obtain a more precise radiographic image of the object 3.

This method applies to simple or multiple energy radiations; in the latter case, it is repeated separately for each of the energies used.

The functional proposed here is not the only one that may be used, and the simpler functional $\Phi d = k\Phi$ (here approaching closer in $\Phi d = k\Phi t$), where k is a constant, could thus give good results for estimating $\Phi d$.

As has been stated, this method is particularly interesting in tomography or bone densitometry, where an in-depth image of the object is reconstructed from a multitude of acquisitions (irradiations) taken around the object by a mobile network of detectors, then by a digital combination of said acquisitions (carried out using techniques that are not covered by the invention). One of the limitations encountered in practice is the excessive dose received by the object; however, we have seen that the method according to the invention makes it possible to reduce the dose required compared to other methods, especially those that impose a double irradiation, to subtract the scattered radiation from the total radiation. It is felt that this advantage will be marked in linear network detector methods (or with superimposed lines in a two dimensional network where one obtains one or several cross-sections (two dimensional images) through the object.

When several acquisitions k are undertaken, the operating method summarised by FIG. 3 may be applied to each of them, an independent estimation of the scattered radiation being made each time. However, situations exist where the scattered radiation could be considered invariable, particularly for objects with rotational symmetry, very frequent in non-destructive control methods. Several of the steps of FIG. 3 then become unnecessary: one could thus make do with the selection of a single imitation 8 for all of the acquisitions k; if necessary, only steps E3, E5, E7 and E8 involving the object need to be repeated for each acquisition. The choice of a simplification of the method by the omission of certain calibrations could be at the discretion of the operator.

The invention claimed is:

1. An object imaging method by multiple acquisitions, the acquisitions consisting in passing a radiation through the object, measuring the radiation having passed through the object, the radiation being attenuated through the object from an initial radiation ($\Phi_o$) to a total measurement radiation ($\Phi_t$ object), and subtracting an estimation of a scattered radiation ($\Phi_d$ object) from the total measurement radiation, the measurement radiation and scattered radiation consisting of values associated to respective parts of the object, and wherein:

for at least one of said acquisitions, values of scattered radiation ($\Phi_d$ imitation) are measured in passing the initial radiation through an imitation (8) of the object, transposition coefficients (K) relating the scattered radiation through the object to the scattered radiation through the imitation (8) are calculated based on the initial radiation ($\Phi_o$), the total measurement radiation ($\Phi_t$ object) through the object and a total measurement radiation through the imitation ($\Phi_t$ imitation), the scattered radiation through the object in estimated with the transposition coefficients and the scattered radiation through the imitation, the values of total measurement radiation through the objects, the values of scattered radiation through the imitation and the transposition coefficients being spread in respective tables comprising corresponding elements so that each of the transposition coefficients is associated to a respective part of the object.

2. Imaging method according to claim 1, characterised in that the imitation (8) is a block of constant thickness and in a homogeneous material, with an attenuation similar to a base material of the object.

3. Imaging method according to claim 1, characterised in that the taking of the measurement table is a selection in a series of scattered diffusion measurement tables, obtained by successively passing the initial radiation through a respective series of imitations of the object, which are blocks of different but constant thickness and in a homogeneous material, having an attenuation similar to a base material of the object.

4. Imaging method according to claim 3, characterised in that the selection comprises an interpolation between two tables of measurements.

5. Imaging method according to claim 3, characterised in that the selection is carried out by comparing a value of the total measurement radiation through the object and a value of the total measurement radiation through the imitations.

6. Imaging method according to claim 5, characterised in that the comparison is carried out for identical rays (13) of the initial radiation through the object and the imitations, only going through the base material of the object.

7. Imaging method according to claim 1, characterised in that it comprises a step of low pass filtering of the transposition coefficients, arranged in a table superposable on the table of measurements.

8. Application of the method according to claim 1 to tomography.

9. Application of the method according to claim 1 to bone densitometry.

10. Application of the method according to claim 1 to non-destructive controls.

11. An object imaging method according to claim 1, wherein the coefficients are computed according to the formula: $K=\Phi_t \log(\Phi_t/\Phi_o)$ object $\Phi_t \log(\Phi_t/\Phi_o)$ imitation.

* * * * *

UNITED STATES PATENT AND TRADEMARK OFFICE
CERTIFICATE OF CORRECTION

PATENT NO.       : 7,031,427 B2                               Page 1 of 1
APPLICATION NO.  : 10/644367
DATED            : April 18, 2006
INVENTOR(S)      : Jean-Marc Dinten et al.

It is certified that error appears in the above-identified patent and that said Letters Patent is hereby corrected as shown below:

Column 5, line 24 please delete "($\Phi$ object)" and insert therefore --($\Phi_t$object)--
Column 6, claim 11, line 36 please delete the formula and insert the following formula
-- $\underline{K = [\Phi_t \log(\Phi_t/\Phi_o)]\ object}$ $[\Phi_t \log(\Phi_t/\Phi_o)]$ imitation--

Signed and Sealed this

Fifth Day of September, 2006

JON W. DUDAS
*Director of the United States Patent and Trademark Office*